United States Patent
Jacobsen et al.

[11] Patent Number: 5,931,647
[45] Date of Patent: *Aug. 3, 1999

[54] VOLUMETRIC PUMP WITH BI-DIRECTIONAL PISTON SEAL

[75] Inventors: Stephen C. Jacobsen; Clark C. Davis, both of Salt Lake City, Utah

[73] Assignee: Sarcos, Inc., Salt Lake City, Utah

[*] Notice: This patent is subject to a terminal disclaimer.

[21] Appl. No.: 08/786,936

[22] Filed: Jan. 23, 1997

Related U.S. Application Data

[63] Continuation-in-part of application No. 08/157,693, Nov. 23, 1993, Pat. No. 5,632,606.

[51] Int. Cl.$^6$ .................................................. F04B 35/04
[52] U.S. Cl. .......................... 417/415; 417/547; 92/168; 277/567
[58] Field of Search ................................. 417/223, 415, 417/416, 417, 545, 547, 549; 92/168; 277/567

[56] References Cited

U.S. PATENT DOCUMENTS

| | | |
|---|---|---|
| 247,360 | 9/1881 | Jay .............................................. 92/168 |
| 695,589 | 3/1902 | Storle . |
| 789,430 | 5/1905 | Jewson . |
| 1,032,187 | 7/1912 | Clifford . |
| 1,460,628 | 7/1923 | Wertz . |
| 1,536,415 | 5/1925 | Beck et al. . |
| 1,815,907 | 7/1931 | Halstead et al. . |
| 2,022,443 | 11/1935 | Stollberg . |
| 2,393,442 | 1/1946 | Yellott et al. . |
| 2,501,707 | 3/1950 | Bent . |
| 2,645,449 | 7/1953 | Gulick . |
| 2,653,580 | 9/1953 | Moore, Jr. . |
| 2,709,118 | 2/1955 | Martin . |
| 2,750,746 | 6/1956 | Brannen . |
| 2,766,701 | 10/1956 | Giraudeau ................................. 92/168 |
| 2,782,801 | 2/1957 | Ludwig . |
| 2,856,961 | 7/1954 | Kruschik . |
| 3,019,739 | 2/1962 | Prosser ....................................... 92/168 |
| 3,095,785 | 7/1963 | Cahill et al. . |
| 3,177,780 | 4/1965 | Anderson . |
| 3,216,332 | 11/1965 | de Chambeau et al. . |
| 3,268,201 | 8/1966 | Little . |
| 3,275,331 | 9/1966 | Mastrobattista et al. . |
| 3,300,703 | 1/1967 | Gold et al. . |
| 3,414,693 | 12/1968 | Watson et al. . |
| 3,463,193 | 8/1969 | Yost . |
| 3,509,890 | 5/1970 | Phillips ................................... 277/152 |

(List continued on next page.)

FOREIGN PATENT DOCUMENTS

| | | |
|---|---|---|
| 1283209 | 12/1960 | France . |
| 855649 | 11/1952 | Germany . |
| 2339937 | 2/1974 | Germany . |
| 119145 | 9/1918 | United Kingdom . |

*Primary Examiner*—Timothy S. Thorpe
*Assistant Examiner*—Ehud Gartenberg
*Attorney, Agent, or Firm*—Thorpe, North & Western, L.L.P.

[57] ABSTRACT

A volumetric pump for administering intravenous fluids to a patient comprises a housing having an elongate cavity therein with an open and a closed end. A resilient sheet of material having two branched portions which form a centrally-located aperture is disposed over the open end of the housing. A pump shaft is slidably disposed through the aperture such that one branched portion toward the cavity and the other branched portion extends away from the housing such that a sphincter seal is formed about the shaft. An inlet conduit leading from a fluid source such as an IV bag passes through the housing into the cavity near one end thereof, and an outlet conduit leading to a fluid sink such as a patient passes through the housing from the cavity near the other end thereof. The shaft is driven back and forth in reciprocating motion, inwardly and outwardly of the cavity, to alternately produce a positive pressure forcing fluid out of the outlet conduit to the fluid sink, and a negative pressure forcing fluid from the fluid source through the inlet conduit.

16 Claims, 1 Drawing Sheet

U.S. PATENT DOCUMENTS

| | | |
|---|---|---|
| 3,510,177 | 5/1970 | Shimula . |
| 3,515,169 | 6/1970 | Berg et al. . |
| 3,552,441 | 1/1971 | Luhleich . |
| 3,648,568 | 3/1972 | Wright . |
| 3,742,822 | 7/1973 | Talbert ................ 92/168 |
| 3,802,805 | 4/1974 | Roeser . |
| 3,847,453 | 11/1974 | Herbert . |
| 4,042,248 | 8/1977 | Williamitis ................ 277/152 |
| 4,055,107 | 10/1977 | Bartley . |
| 4,085,941 | 4/1978 | Wilkinson et al. . |
| 4,089,349 | 5/1978 | Schenk . |
| 4,095,566 | 6/1978 | Fox et al. . |
| 4,128,227 | 12/1978 | Blomqvist . |
| 4,159,024 | 6/1979 | Getman . |
| 4,197,786 | 4/1980 | Pillon . |
| 4,222,575 | 9/1980 | Sekiguchi et al. . |
| 4,241,644 | 12/1980 | Schertler . |
| 4,280,741 | 7/1981 | Stoll ................ 277/152 |
| 4,384,511 | 5/1983 | Mefferd ................ 92/168 |
| 4,392,034 | 7/1983 | Payne . |
| 4,433,795 | 2/1984 | Maiefski . |
| 4,437,821 | 3/1984 | Ogawa ................ 277/152 |
| 4,448,425 | 5/1984 | von Bergen . |
| 4,449,717 | 5/1984 | Kitawaki et al. . |
| 4,468,170 | 8/1984 | Hanset . |
| 4,549,718 | 10/1985 | Seger . |
| 4,627,795 | 12/1986 | Schmitz-Montz . |
| 4,637,295 | 1/1987 | Powers et al. ................ 277/152 |
| 4,674,965 | 6/1987 | Hasegawa et al. . |
| 4,721,133 | 1/1988 | Sundblom . |
| 4,723,755 | 2/1988 | Ishigaki . |
| 4,751,867 | 6/1988 | Johnsson et al. . |
| 4,759,553 | 7/1988 | Goodman et al. . |
| 4,804,913 | 2/1989 | Shimizu et al. . |
| 4,900,883 | 2/1990 | Brame et al. . |
| 4,974,755 | 12/1990 | Sonntag . |
| 4,975,679 | 12/1990 | Ballyns . |
| 5,104,374 | 4/1992 | Bishko et al. . |
| 5,140,113 | 8/1992 | Machado . |
| 5,144,882 | 9/1992 | Weissgerber . |
| 5,199,718 | 4/1993 | Niemiec . |
| 5,267,721 | 12/1993 | Stroh . |
| 5,380,017 | 1/1995 | Leeuwenburg et al. . |
| 5,429,602 | 7/1995 | Hauser . |
| 5,440,968 | 8/1995 | Sekine . |
| 5,467,689 | 11/1995 | Carlin et al. . |

VOLUMETRIC PUMP WITH BI-DIRECTIONAL PISTON SEAL

BACKGROUND OF THE INVENTION

This is a continuation-in-part of U.S. patent application Ser. No. 08/157,693, filed Nov. 23, 1993, now U.S. Pat. No. 5,632,606 entitled VOLUMETRIC PUMP/VALVE.

This invention relates to a lightweight, inexpensive and therefore disposable volumetric pump, suitable for a variety of uses including medical systems such as intravenous (IV) therapy systems and the like.

The intravenous administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently requires the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

The disposable non-electric pumps generally consist of small elastomeric bags within a hard shell container, in which the bags are filled with IV solution under pressure. The pressure generated by the contraction of the elastomeric bag forces the IV solution through a fixed orifice at a constant flow rate into the patient's vein. Although these pumps are much less expensive than the electronic pumps and eliminate the need for maintenance (since they are discarded after every use), their drawbacks include the lack of monitoring capability, the lack of the ability to select different flow rates, limited fluid capacity, and still relatively high cost for a disposable product.

SUMMARY OF THE INVENTION

It is an object of the invention to provide a new and improved volumetric pump which is especially suitable for use in IV administration sets, other medical systems, and the like.

It is a further object of the invention to provide such a pump which is easy to manufacture and utilizes low cost parts.

It is also an object of the invention to provide such a pump configured to sweep bubbles from the pump cavity during operation.

It is another object of the invention to provide such a pump design in which the need for tight tolerances is minimized.

It is yet another object of the invention to provide such a pump which is efficient and reliable.

It is an additional object of the invention to provide such a pump which may be readily miniaturized.

The above and other objects of the invention are realized in a specific illustrative embodiment of a pump which utilizes a simple circumferential sphincter seal, to retain and prevent loss or leaking of the fluid being pumped. One illustrative embodiment of the invention includes a housing defining an elongate cavity therein, with an opening on one side of the housing adjacent to and in communication with the one end, the other end being closed. Also included is a resilient sheet of material disposed over the opening in the housing, with the sheet including an aperture positioned in alignment with the cavity at the one end thereof. The aperture is defined by two branches extending from the sheet to circumscribe the aperture. One branch of the sheet extends toward the cavity and the other branch extends away from the housing. An elongate shaft is slidably disposed in the aperture so that one end of the shaft extends into the cavity and the other end extends out of the housing. The aperture has substantially the same cross-sectional shape as that of the shaft, and the same cross-sectional dimensions or smaller.

An inlet is provided in the housing, through which fluid from a fluid source may flow into the cavity, and an outlet is also provided in the housing, through which fluid may flow from the cavity to a fluid sink.

The resilient sheet of material surrounds and grips the shaft to provide a sphincter seal which substantially prevents fluid from flowing through the aperture but allows the shaft to slide longitudinally therein. As the shaft moves in either direction the branches of the sheet cooperate to alternatively strip the shaft of fluids and act as primary and secondary seals.

When the shaft is moved in a direction outwardly of the housing, a negative pressure is produced in the cavity to draw in fluid through the inlet, and when the shaft is moved further into the cavity, a positive pressure is produced in the cavity to force fluid from the cavity through the outlet. Valves may be provided in or near the inlet and outlet to allow fluid only to flow into the cavity through the inlet and out of the cavity through the outlet.

A variety of driver mechanisms and control methods may be provided to cause the shaft to reciprocate within the cavity to produce the pumping action, including ratchet drives, magnetic linear step motors, rotary-to-linear crank drives, screw drive mechanisms, etc.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE DRAWINGS

Figure 1:
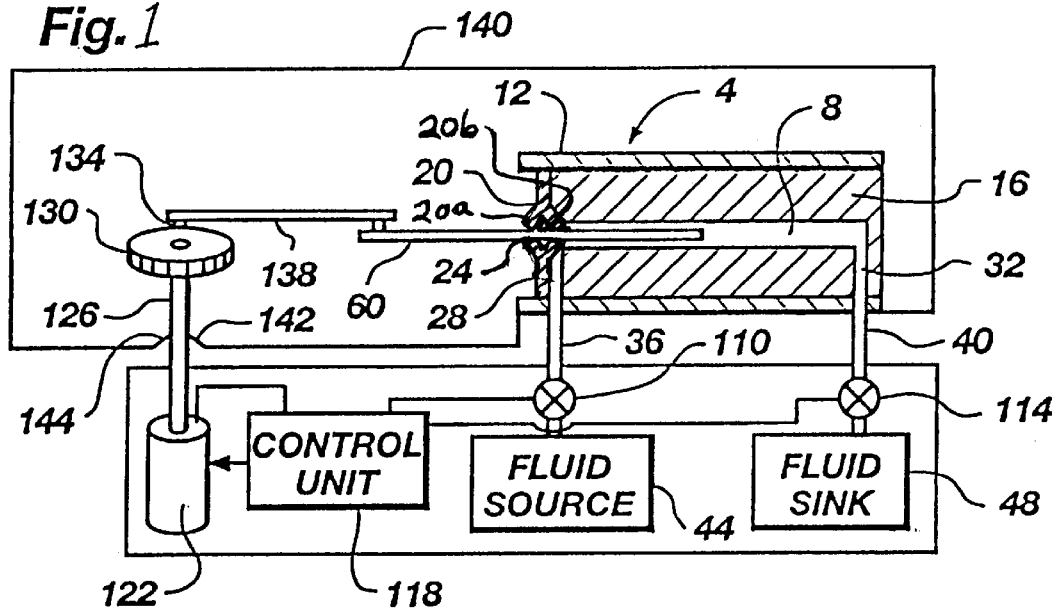
FIG. 1 is a side, cross-sectional view of a volumetric pump, using a sphincter seal, made in accordance with the principles of the present invention.

Referring to FIG. 1, there is shown a perspective view of a volumetric pump made in accordance with the present invention to include a generally elongate housing 4, formed with an elongate cavity 8 therein. The housing 4 might illustratively be formed with an exterior shell 12 made of metal or plastic, and an interior filler 16 disposed against the shell 12, with the cavity 8 formed centrally therein. The filler could similarly be metal or plastic. The cross-sectional shape of the housing 4 could be square, round, etc.

Disposed in one end of the housing 4 is a resilient sheet of material 20 made, for example, of latex rubber, silicone rubber, nitrile rubber, polytetrafluoroethylene, polyurethane, EPDM, etc. The sheet of material 20 fills the end of the housing 4 to prevent communication between the outside of the housing and the cavity 8 except through an aperture 24 positioned in line with the cavity 8.

An inlet conduit 36 is formed in the housing 4 generally adjacent to the sheet of material 20, to communicate with the cavity 8, and an outlet conduit 40 is similarly formed in the housing to communicate with the cavity at the other end thereof. (Of course, the inlet and outlet could be positioned at other locations or even combined, with check valves used for controlling the direction of flow.) The conduits 36 and 40 couple the cavity to a fluid source 44 and a fluid sink 48 respectively. Valves 110 and 114 are disposed respectively in conduits 36 and 40 and operate (open or close) in response to control signals from control unit 118, to allow fluid to flow from the fluid source 44 into the cavity 8 and prevent the reverse flow, and to allow fluids to flow from the cavity 8 to the fluid sink 48 and prevent the reverse flow. The fluid source 44 could be any source of fluid which it is desired to be pumped to fluid sink 48, such as an IV administration set which includes a bottle of fluid to be administered to a patient, with the fluid source 44 being the bottle and the fluid sink 48 being the patient receiving the fluid. Of course, as will be evident upon further discussion, the fluidic pump of FIG. 1 could be used in a variety of environments.

An alternative arrangement for connecting the pump to the fluid source 44 and fluid sink 48 would be to employ a single conduit accessing the cavity 8, with a (check) valve connecting the fluid source to the single conduit and another (check) valve connecting the single conduit to the fluid sink. It will be evident later when discussing the pumping action of the pump that upon the intake stroke of the pump, fluid would flow from the fluid source through the (check) valve and single conduit to the chamber 8 and upon the pump stroke, fluid would flow from the chamber through the other (check) valve to the fluid sink.

An elongate shaft or plunger 60 is disposed in the aperture 24 of the sheet of material 20 to extend at least partially into the cavity 8 of the housing 4. The shaft 60 may have a circular cross section and have a somewhat smaller circumference than that of the cavity 8 so that the shaft may be moved in a reciprocating fashion back and forth in the aperture 24 and cavity 8 with little or no abrasion or resistance with or from the material forming the cavity.

The aperture 24 in the resilient sheet of material 20 is defined by two branches or flanges 20a and 20b of the sheet 20. The branches, in the preferred embodiment are formed integrally with the sheet 20. Branch 20a extends in the general direction of the exterior of the housing 4 and toward the shaft 60. Branch 20b extends in the general direction of the cavity 8. Branches 20a and 20b combine to circumscribe the aperture 24 and, consequently, the shaft 60 disposed therein. The aperture 24 is preferably shaped similarly to the cross-sectional shape of the shaft 60 and is preferably the same or slightly smaller in size in order to completely surround and grip the shaft to form a sphincter seal and prevent fluid from escaping the cavity 8.

As the aperture is formed in the resilient sheet of material 20, the aperture conforms to the shape of the shaft 60 even if their shapes are not identical, though it will be obvious to those skilled in the art that the more the shapes differ, the less effective the seal will be.

The branches 20a and 20b are resilient enough to seal the aperture when the shaft 60 is disposed therein. If the branches are too short they will not properly distend away from each other in a tight fit with the shaft. If they are too long, they will either distend so far that the mid-length of each branch will be in contact with the shaft and its end will not be as rigidly in contact as desired. This contact of the ends of the branches with the shaft is important to maximize the branches' ability to strip impurities and liquid from the shaft as it reciprocates. It has been found optimal to minimize the distance between the sheet proper and the shaft, and to make the branches a length that disposes them at an angle of about 5°–50° to the shaft.

The control unit 118 in addition to controlling valves 110 and 114, also controls operation of an electric motor 122 whose drive shaft 126 is coupled to a drive wheel 130. As the motor 122 operates to rotate the drive shaft 126, the wheel 130 is rotated. A drive nipple 134 is mounted near the perimeter of the drive wheel 130 and is pivotally coupled to one end of a drive shaft 138 which, in turn, is pivotally coupled at its other end to the free end of the pump shaft 60. As the drive wheel 130 is caused to rotate, the drive shaft 138 is caused to reciprocate back and forth, and, in turn, causes the shaft 60 to reciprocate in the cavity 8.

A second housing 140 is provided in the preferred embodiment around the housing 4, pump shaft 60, drive shaft 138, drive wheel 130, and a portion of the drive shaft 126, to seal the components from outside contamination or interference. The housing 140 preferably comprises rigid material such as steel or plastic except around the drive shaft 126, where it comprises a sheet of resilient material 142, similar to the sheet 20, with an aperture 144 formed therein to create a sphincter sterility seal on the drive shaft 126 similar to the seal of the sheet 20 around the pump shaft 60. However, in the case of the drive shaft 126, the sheet 142 at the aperture 144 seals the drive shaft 126 during rotational, rather than reciprocal, movement.

In operation, the control unit 118 causes the motor 122 to operate and rotate, with the angular position of the drive shaft 126 being fed back to the control unit. Based on the angular position of the drive shaft 126 and thus the drive wheel 130, the control unit will cause valves 110 and 114 to alternately open and close to allow fluid to flow from the fluid source 44 into the cavity 8 on the withdrawal stroke or movement of the shaft 60, and allow fluid to flow from the cavity 8 to the fluid sink 48 on the pump stroke of the shaft 60. In effect, direct control of the opening and closing of the valves 110 and 114 is provided to ensure effective pumping of fluid from the fluid source 44 to the fluid sink 48 by preventing free flow caused when both valves are open at the same time (which might occur, for example, if the fluid source were an IV bag and IV bag was squeezed). The control unit 118 might illustratively be any conventional microprocessor used for controlling operation of electrical equipment.

One advantage to the pump shown in FIG. 1 is that the shapes of the plunger and cavity cause gas bubbles to be swept out of the cavity with each stroke of the plunger, instead of accumulating in the cavity, especially around the seal made in the sheet 20. This allows for greater volumetric accuracy in the pumping action.

As the shaft 60 reciprocates within the cavity 8 to provide the described pumping action, ancillary forces are created upon the seal formed by the aperture 24 and the reciprocating shaft 60. These ancillary forces are an alternating pressure differential which will be described as high and low pressure events within the cavity 8. As the shaft 60 moves outwardly, the pressure within the cavity 8 decreases. But for the seal, ambient air would be urged into is the cavity. Branch 20*a* of the sheet 20 is urged by this pressure differential in the direction of the shaft 60, thereby securing the seal even more tightly. Branch 20*b* of the sheet 20 strips fluid from the shaft as it exits the chamber. During the entry of the shaft 60 into the cavity 8, a high pressure develops within the cavity. This high pressure urges branch 20*b* in the direction of the shaft 60, thereby securing the seal even more tightly and preventing loss of the fluid. Branch 20*a* also strips the shaft 60 of any particulate or other impurities as it enters the cavity. Branches 20*a* and 20*b* of the sheet 20 act in a residual and backup manner to perform the described functions of the other; however, their primary function is enhanced by their articulation in the direction of the inwardly moving shaft and ambient air (branch 20*a*) and outwardly moving shaft and cavity (branch 20*b*) respectively. Branches 20*a*, 20*b* and shaft 60, form a complex which prevents extensive distention of sheet 20.

Figure 2:
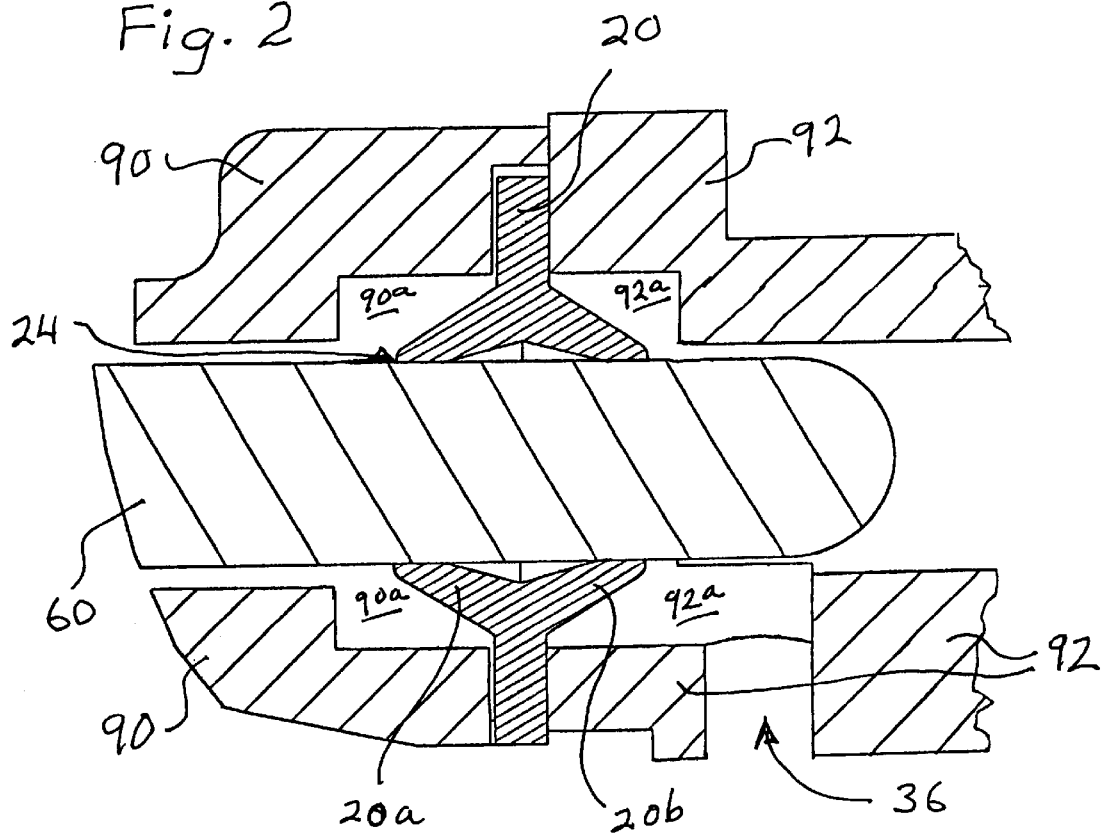
FIG. 2 is a fragmented, side, cross-sectional view of an embodiment of front and rear supports for the sphincter seal.

FIG. 2 shows a fragmented, side, cross-sectional view of the shaft 60, the aperture 24 in the resilient sheet 20, with the addition of forward and rear seal supports 90 and 92. The supports 90 and 92 allow for greater positive or negative fluid pressure in the cavity 8 by supporting the sheet 20 at the aperture 24 so that it does not distend with the movement of the shaft 60 into the cavity (to thus stretch and degrade the resilient material and damage the seal), or collapse with the movement of the shaft 60 away from the cavity 8. It will be appreciated that a more rigid complex between branches 20*a* and 20*b* and shaft 60 could also be used for this purpose, however supports as described allow an even more resilient sheet material to be used. Greater fluid pressure in the cavity exacerbates the problems of distending and collapsing the sheet 20, which the supports 90 and 92 help prevent.

The rear support 92 preferably comprises an inflexible flat plate with an aperture 92*a* formed therein. The aperture 92*a* is preferably similar in shape and slightly larger in size than the larger part of branch 20*b* to allow free movement of the shaft therein, and is located close to the sheet 20. During movement of the shaft 60 into the cavity 8, the friction of the shaft 60 against the branches 20*a* and 20*b* tends to cause the sheet 20 to distend toward the cavity 8. The sheet 20, however, contacts the support 92 before distending enough to damage the material or loosen the seal. Like the support 92, the support 90 preferably comprises a plate with an aperture 90*a* formed therein. Apertures 90*a* and 92*a* allow the free functioning of branches 20*a* and 20*b*, but allow supports 90 and 92 to provide desired support to sheet 20.

The embodiments of the invention described herein are only examples of how the invention may be applied to specific devices. Modifications and variations of, for example, materials used, sizes and shapes of components, and equivalent structures will be apparent to those skilled in the art while remaining within the scope of the invention.

What is claimed is:

1. A pump for pumping fluids from a fluid source to a fluid sink comprising
    a housing defining an elongate cavity therein, with an opening on one side of the housing adjacent to and in communication with one end of the cavity,
    a sheet of resilient material disposed over the opening in the housing, said sheet including first and second branches circumscribing and defining an aperture positioned in alignment with the cavity at said one end thereof,
    an elongate shaft slidably disposed in the aperture substantially orthogonal to the sheet so that one end of the shaft extends into the cavity and the other end extends out of the housing, said aperture having substantially the same cross-sectional shape as that of the shaft, and the same cross-sectional dimensions or smaller, such that the first and second branches are in contact with the shaft,
    inlet means for conveying fluid from the fluid source into the cavity,
    outlet means for carrying fluid from the cavity to the fluid sink, and
    actuation means for causing the shaft to reciprocate longitudinally in the cavity, sliding back and forth in the aperture, to alternately produce a negative pressure and positive pressure in the cavity,
    support means on each side of the sheet of resilient material adjacent the aperture for contacting and preventing distending and collapsing of the sheet of material as the shaft slides back and forth in the aperture.

2. A pump as in claim 1 wherein the first branch extends into the cavity at an angle of between 50° and 50° to the shaft, and the second branch extends away from the cavity at an angle of between 50° and 50° to the shaft.

3. A pump as in claim 1 wherein said sheet of material is selected from the group consisting of latex rubber, silicone rubber, nitrile rubber, polytetrafluoroethylene, polyurethane and EPDM.

4. A pump as in claim 1 wherein the inlet means is disposed near said one end of the cavity, and wherein the outlet means is disposed near said other end of the cavity.

5. A pump as in claim 1 wherein the dimensions of the cross-section of the aperture are smaller than the dimensions of the cross-section of the shaft.

6. A pump as in claim 1 wherein said inlet means includes
    a first conduit for conveying fluid from the fluid source to the cavity, and
    first check valve means disposed in the first conduit for allowing the flow of fluid from the fluid source to the cavity, and for preventing the flow of fluid from the cavity to the fluid source,
and wherein said outlet means includes
    a second conduit for carrying fluid from the cavity to the fluid sink, and
    second check valve means disposed in the second conduit for allowing the flow of fluid from the cavity to the fluid sink, and for preventing the flow of fluid from the fluid sink to the cavity.

7. A pump as in claim 1 wherein said inlet means and outlet means include
    a conduit coupled to the cavity,
    first valve means coupling fluid source to the conduit to allow the flow of fluid from the fluid source only to the conduit and cavity, and
    second valve means coupling the conduit to the fluid sink to allow the flow of fluid only from the cavity and conduit to the fluid sink.

8. A pump as in claim 1 wherein said inlet means includes
    a first conduit for conveying fluid from the fluid source to the cavity, and normally closed valve means responsive to said actuation means causing production of a negative pressure in the cavity for opening to allow the flow of fluid from the fluid source to the cavity,
and wherein said outlet means includes
    a second conduit for carrying fluid from the cavity to the fluid sink, and normally closed valve means responsive to said actuation means causing production of a positive pressure in the cavity for opening to allow the flow of fluid from the cavity to the fluid sink.

9. A pump as in claim 8 wherein the first conduit and second conduit comprise a single conduit.

10. A pump for pumping fluids from a fluid source to a fluid sink comprising a housing defining an elongate cavity therein, with an opening on one side of the housing adjacent to and in communication with one end of the cavity, the other end being closed, a resilient sheet of material disposed over the opening in the housing and having an aperture formed therein and defined by flange means formed in the sheet, said flange means including first and second branches, said first branch extending toward the cavity and said second branch extending away from the cavity, said first and second branches circumscribing the aperture positioned in alignment with the cavity at said one end thereof, an elongate shaft slidably disposed in the aperture so that one end of the shaft extends into the cavity and the other end extends out of the housing, said aperture having substantially the same cross-sectional shape as that of the shaft, and the same cross-sectional dimensions or smaller, inlet means for conveying fluid from the fluid source into the cavity when a negative pressure is produced therein, outlet means for carrying fluid from the cavity to the fluid sink when a positive pressure is produced in the cavity, and actuation means for causing the shaft to reciprocate longitudinally in the cavity, sliding back and forth in the aperture, to alternately produce a negative pressure and positive pressure in the cavity, support means on each side of the sheet of resilient material adjacent the aperture for contacting and preventing distending and collapsing of the sheet of material as the shaft slides through the aperture.

11. A pump as in claim 10 wherein said resilient sheet of material is polymeric.

12. A pump as in claim 10 wherein said resilient sheet of material is a material selected from the group consisting of latex rubber, silicone rubber, nitrile rubber, polytetrafluoroethylene, polyurethane and EPDM.

13. A pump as in claim 11 wherein the inlet means is disposed near said one end of the cavity, and wherein the outlet means is disposed near said other end of the cavity.

14. A pump as in claim 10 wherein the dimensions of the cross-section of the aperture are smaller than the dimensions of the cross-section of the shaft.

15. A pump as in claim 10 wherein said inlet means includes a first conduit for conveying fluid from the fluid source to the cavity, and first valve means disposed in the first conduit for allowing the flow of fluid from the fluid source to the cavity, and for preventing the flow of fluid from the cavity to the fluid source, and wherein said outlet means includes a second conduit for carrying fluid from the cavity to the fluid sink, and second valve means disposed in the second conduit for allowing the flow of fluid from the cavity to the fluid sink, and for preventing the flow of fluid from the fluid sink to the cavity.

16. A pump as in claim 10 wherein said inlet means and outlet means comprise a conduit connected to the cavity, first valve means for conveying fluid from the fluid source to the conduit and cavity, and second valve means for conveying fluid from the cavity and conduit to the fluid sink.

* * * * *